United States Patent [19]

Quick

[11] 4,005,166

[45] Jan. 25, 1977

[54] PROCESS OF MOLDING A CATHETER

[75] Inventor: James R. Quick, Warwick, N.Y.

[73] Assignee: International Paper Company, New York, N.Y.

[22] Filed: May 27, 1975

[21] Appl. No.: 580,881

[52] U.S. Cl. .............................. 264/154; 264/278; 264/328

[51] Int. Cl.² .......................................... B29C 1/14

[58] Field of Search ............ 264/328, 278, 97, 154

[56] References Cited

UNITED STATES PATENTS

| | | | |
|---|---|---|---|
| 2,314,262 | 3/1943 | Winder | 264/154 |
| 2,367,235 | 1/1945 | Morin | 264/328 X |
| 2,465,799 | 3/1949 | Gravesen | 264/328 X |
| 3,142,716 | 7/1964 | Gardener | 264/278 X |
| 3,311,690 | 3/1967 | Fischer | 264/278 |
| 3,363,040 | 1/1968 | Aoki | 264/278 |
| 3,442,987 | 5/1969 | Sentementes | 264/343 X |
| 3,477,101 | 11/1969 | Fritsch | 264/328 X |
| 3,910,743 | 10/1975 | Farrell | 264/97 X |

Primary Examiner—Richard R. Kucia
Attorney, Agent, or Firm—A. L. Michaelsen

[57] ABSTRACT

Disclosed is an apparatus and process for the molding of hollow articles. The apparatus comprises a mold cavity with a wire longitudinally disposed therein. A follower is slidably disposed about the wire in close abutment with both the wire and inside wall of the mold cavity. The follower is preferably disposed in the mold cavity toward its proximal end so as to provide an annular space between the wire and inside wall of the mold. In practice, material to be molded is injected into the annular space at the proximal end of the mold cavity and flows longitudinally toward the distal end of the mold cavity while pushing the follower along the wire ahead of it.

9 Claims, 9 Drawing Figures

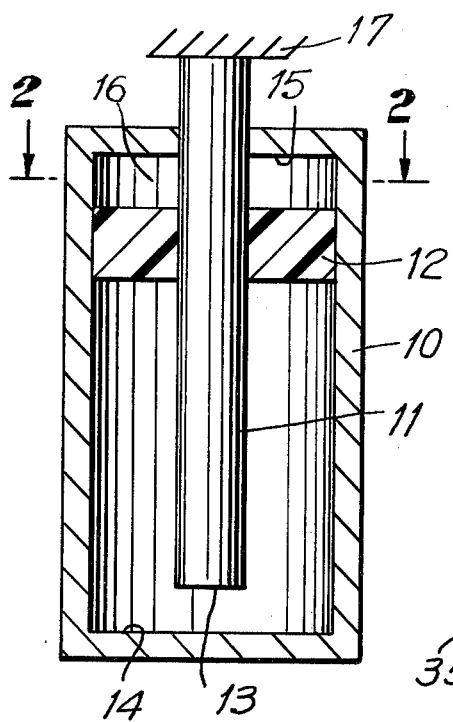
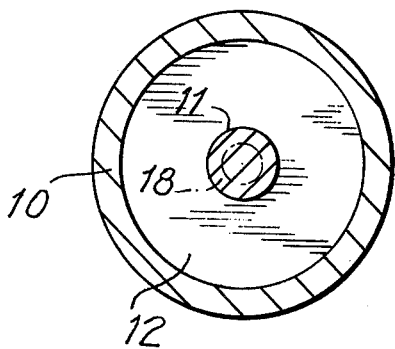
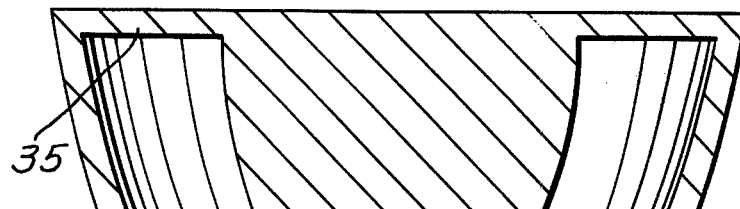
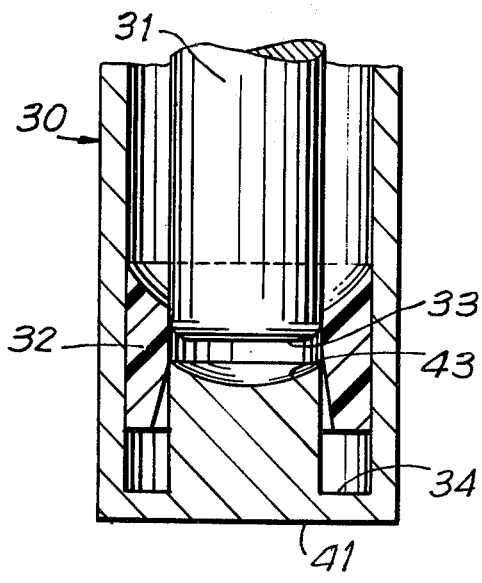
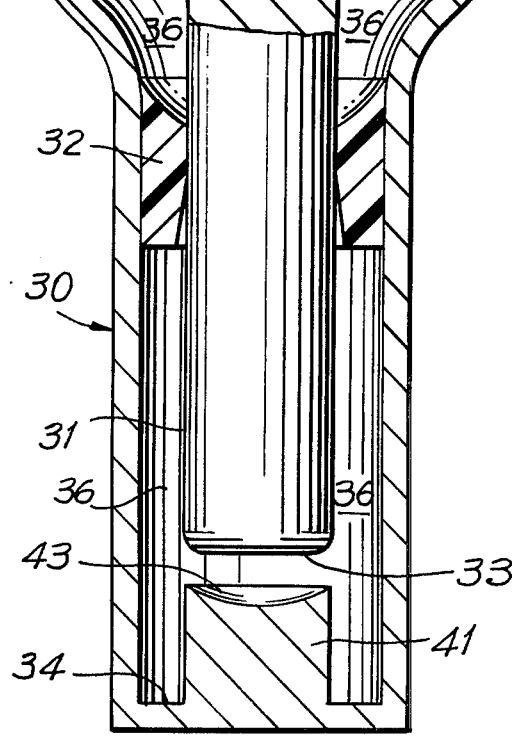

PROCESS OF MOLDING A CATHETER

BACKGROUND OF THE INVENTION

This invention relates to a molding process for producing hollow articles. In the past, hollow articles have been produced by a variety of dipping, molding and extrusion apparatus and processes. However, each of these prior art processes have suffered from disadvantages that are substantially overcome by the present process.

In the dipping processes known in the prior art, a wire is dipped into a liquified material to be formed into the hollow article. With each dip of the wire more product from the bath adheres to the coated wire until eventually the desired amount of material is built up onto the wire. Then the material coated on the wire is sufficiently hardened so as to permit the hollow article surrounding the wire to be peeled or stripped therefrom. One disadvantage of the dipping process is the large number of dips and great amount of time sometimes required to build up the desired amount of material on the wire. Additionally, when the hollow article to be manufactured requires small diameter wires, many materials are too viscous in a liquified state for the wire to be dipped therein without bending of the wire.

As with the above described prior art dipping processes, other prior art processes also have disadvantages. For instance, extrusion processes are not advantageously employed to obtain products with a closed end. Further, while prior art molding processes may be employed to obtain products with closed ends, these processes are generally not advantageously employed when the article is relatively long and slender. The reason for this is that the portion of the mold defining the hollow portion of the final product is often unstable and bends at the high pressures employed in the molding process.

The process of my invention may be employed to produce hollow products from a wide variety of materials including materials which are too viscous in a liquid state to be used to produce hollow articles by prior art dipping processes. Additionally, the process of my invention may be employed to obtain hollow products with one of the ends closed by a tip. Finally, the process of my invention may be used to manufacture hollow bodies which are relatively long and slender.

SUMMARY OF THE INVENTION

The apparatus used in the process of my invention broadly comprises a mold cavity with a first wire longitudinally disposed therein. A follower is slidably disposed about the first wire in close abutment with both the wire and inside wall of the mold cavity. The follower is preferably disposed about the first wire close to the proximal end of the cavity so as to provide an annular space between the wire and inside wall of the mold cavity. Upon injection of material into the mold cavity, said material flows longitudinally toward the distal end of the mold cavity pushing the follower ahead of it. In this manner the wire is maintained in the desired position in the mold cavity during the injection molding process.

The process of my invention may be particularly adapted to form hollow articles with closed tips. In this embodiment of my invention, the first wire terminates proximally of the distal end of the mold and a second wire is provided in aligned relationship with the first wire at the distal end of the cavity. The second wire is spaced from the end of the first wire in such a manner that when the follower reaches the distal end of the first wire and continues to move distally in the mold cavity the follower initially engages with the second wire while still partially engaged with the first wire thereby bridging the space between the first wire and second wire. As the follower continues distally along the longitudinal axis of the mold cavity it disengages the first wire and continues along the second wire to the distal end of the cavity. Once the follower disengages the first wire, the injected material flows inwardly across the entire cross section of the mold cavity thereby forming the tip of the hollow article. Desirably, the proximal ends of the follower and second wire are concave so as to provide a rounded tip.

During the molding process the mold cavity is desirably maintained at a suitable temperature so that shortly after the follower reaches the distal end of the cavity the material injected into the cavity will be cured or hardened. After the molded material is sufficiently cured or hardened the mold is opened and the hollow article is stripped or peeled from the first wire.

BRIEF DESCRIPTION OF THE DRAWINGS

FIG. 1 shows the mold employed according to one embodiment of my invention.

FIG. 2 shows a cross section of FIG. 1 along line 2—2.

FIG. 3 shows the mold employed in another embodiment of my invention.

FIG. 4 shows the arrangement of the follower and wires during one stage of an embodiment of my invention.

DESCRIPTION OF THE PREFERRED EMBODIMENTS

Figure 5:
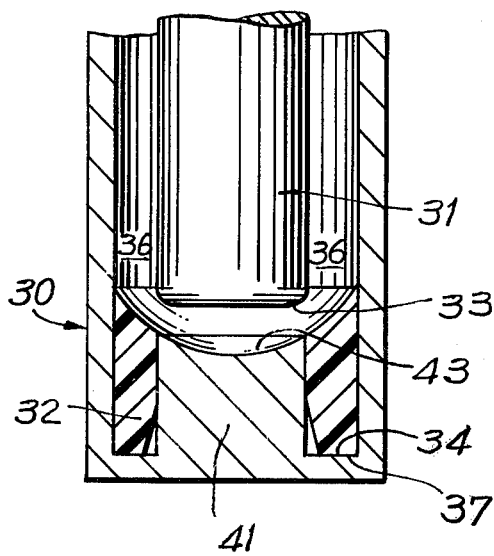
FIG. 5 shows the arrangement of the follower and wires at the completion of one embodiment of my invention.

Referring now to FIG. 1 there is shown in cross section mold 10 with wire 11 and follower 12 provided therein. As shown in FIG. 1, wire 11 is hung from a source 17 and terminates at 13 close to the distal end 14 of mold 10. However, it is to be understood that any suitable means for providing the wire in the mold cavity may be employed in my invention. For instance, the wire 11 may be imbedded into or adhesively attached to the distal end 14 of mold 10.

As shown in FIG. 1, follower 12 fits snugly into annular space 16 in close abutment with wire 11 and the inside of mold 10. As is perhaps best seen from FIG. 2, the follower 12 fills the entire cross section between the inside wall of mold 10 and wire 11. The follower 12 fits into annular space 16 so that it will not drop to the distal end 14 of mold 10 due to its own weight. Additionally, the follower 12 is fitted into annular space 16 so that in use substantially no material injected into the mold will flow into the spaces between the follower 12 and the inside wall of mold 10 and wire 11. In practice, the maximum size of the spaces may vary slightly depending on the material molded, but clearances less than about 0.005 inches are preferred with clearances less than about 0.001 inches being most preferred.

At the start of the process the follower 12 is located proximally of the distal end 14 of the mold 10. While some of the advantages of the present invention may be obtained when the follower is located elsewhere, it is preferred that the proximal end of the follower 12 be located somewhere along the first 20% of the distance between the proximal end 15 and distal end 14 of the mold 10 and most preferably along the first 1% of this distance.

With the wire 11 and follower 12 suitably arranged in mold 10, material to be molded, e.g., catalyzed silicone rubber, is injected into annular space 16 by suitable means (not shown) proximally of the proximal end 15 of mold 10, preferably at about 2500 to 40,000 psig and most preferably at about 4000–10,000 psig. Suitable means for injecting the silicone rubber into the mold are well known to those skilled in the art. For example, reciprocating screw injection molding machines can be equipped with rubber injection units and employed in the present invention.

Preferably, the catalyzed silicone rubber injected has been freshened, e.g., on a two roll mill, to eliminate any structuring of the silicone rubber that may have occurred during storage and to soften the composition sufficiently for the molding process. During the freshening operation suitable cross linking agents or catalysts may be admixed with the silicone rubber. Both in the premixing device and molding machine, the temperature of the catalyzed silicone rubber must be kept sufficiently low so as to prevent the activation of the catalyst but at the same time sufficiently warm so that the material will flow easily when injected into the mold. The temperatures that should be maintained, of course, will vary with the silicone rubber material being molded and the specific catalyst system employed, but for known peroxide catalysts the temperatures of the silicone rubber injected into annular space 16 is preferably maintained at about 80° F. to 130° F.

It is to be understood that any type of catalyst may be employed with the silicone rubber of the present invention, but the preferred catalysts are peroxide catalysts, with the most preferred being di (2,4-dichlorobenzoyl) peroxide, dibenzoyl peroxide, dicumyl peroxide, 2,5-dimethyl-2,5-di (t-butylperoxy) -hexane or mixtures thereof. Similarly, the amount of cross linking agent or catalyst employed may be widely varied with the most preferred amounts being 0.5–1.5 parts by weight di (2,4- dichlorobenzoyl) peroxide, 0.5 to 1.0 parts by weight dibenzoyl peroxide, 0.5 to 1.6 parts by weight dicumyl peroxide, and 0.4 to 1.5 parts by weight 2,5-dimethyl-2,5 di(t-butylperoxy)hexane, all parts per 100 parts by weight silicone rubber.

The catalyzed silicone rubber injected into the mold cavity flows through annular space 16 pushing follower 12 ahead of it until the distal end of follower 12 reaches the distal end 14 of mold 10. At this point, in the embodiment of FIG. 1, the follower 12 is still partially on wire 11. As a result a hollow article that is open at both ends is molded about wire 11. As the follower 12 moves longitudinally through the mold 10, it maintains and stabilizes the wire at the desired distance from the inside wall of mold 10. Small air vents are located along the length of mold 10 as to relieve air pressure that would otherwise build up as the silicone rubber and follower 12 move toward the distal end 14 of mold 10.

The temperature of the mold 10 is preferably maintained during processing in a range which will activate the catalyst system in the silicone rubber. The temperature of mold 10 and rate of flow in annular space 16, of course, must be regulated so that the silicone rubber does not cure to the extent that precludes complete flow of silicone rubber into annular space 16. The temperature is preferably maintained, however, so as to minimize the cure time after complete injection of silicone rubber into mold 10. The mold 10 may be maintained at the desired temperature in a variety of ways. For example, one suitable method comprises supplying heat from electric heating elements located in the walls of mold 10. Another suitable method for maintaining the mold at a suitable temperature comprises circulating a hot fluid, e.g., hot oil, through channels in the walls of the mold. While precise temperatures will vary with the particular silicone rubber composition and process employed, suitable mold temperatures for di(2, 4 dichlorobenzoyl) peroxide or dibenzoyl peroxide are about 240°–270° F, for dicumyl peroxide about 310°–360° F., for 2, 5-dimethyl-2, 4di(t-butylperoxy) hexane about 330°–360° F. and for mixtures of the above catalysts the highest temperature of any constituent of the mixture.

Once the silicone rubber is sufficiently cured, the mold 10 is opened and the silicone rubber hose-like article may be manually peeled or stripped from the wire 11. Before stripping the silicone rubber hollow article from the wire, the hollow article and the wire 11 may be removed from the mold 10 as a unit. In such a case the mold 10, of course, should be designed so that the wire 11 can be easily removed and reinstalled each time an article is molded. It may also be desirable to soak the coated wire in a suitable organic solvent, e.g., toluene, in order to swell the hollow article before the article is stripped from the wire. In the swelled state the hollow article then may be more easily stripped from the wire. After the article is stripped from the wire the organic solvent is then evaporated and the silicone rubber article will then shrink back to normal size.

Further regarding the wire 11 which is employed in the present invention, it is preferred that the wire be solid so as to minimize bending which may occur during the injection molding process. However, the wire may be hollow as represented by dotted line 18 in FIG. 2. The wire 11 may be made from any material which is capable of withstanding the side stresses which may occur during the molding process of the present invention. Preferably, the wire is hardened steel which has been polished and coated with a release agent so as to enhance the sliding of the follower through annular passageway 16 and to aid in the removal of the hollow article produced by the injection molding process. The choice of release agents will depend on the particular composition being molded, but with silicone rubber the preferred release agents are fluorocarbon polymers applied as dispersions of fine particles in a suitable vehicle. The most preferred release agent for silicone rubber is Vydax, a dispersion of a telomer of tetrafluoroethylene in a vehicle of trichlorotrifluoroethylene. The preferred release agents employed are fluorocarbons such as Vydax. As shown in FIG. 2 the mold 10 and wire 11 are cylindrical. However, it is to be understood that other configurations of each are contemplated as within the scope of my invention.

The follower 12 may be made from any material which is capable of sliding through annular passageway 16 as described above. The preferred materials that may be employed are case hardened steel coated with the same release agent coated on wire 11, or a plastic, e.g., poly(tetrafluoroethylene) which is lubricated by the release agent coated on wire 11. It is to be understood, however, that followers made from other materials may be employed within the scope of the present invention.

Referring now to FIG. 3 there is shown an apparatus for producing a closed ended hollow article according to the present invention. More specifically, and for purposes of illustration, there is shown an apparatus for producing a nonretention urinary catheter according to the present invention.

Urinary catheters, as is well known to physicians, are used in the treatment of individuals who have lost control of their urinary function. One generally accepted medical practice involves inserting a tube or catheter up the urinary passage until the remote or distal end is located within the bladder. The near or proximal end of the catheter remains outside the body. Often the most proximal end of the catheter is in the shape of a funnel. The funnel is in communication with a path or drainage lumen that is provided along the longitudinal axis of the catheter. The distal end of the catheter contains a hole in communication with the drainage lumen such that in use the bladder may drain through the hole into the drainage lumen and out through the funnel into a suitable receptacle. While the invention is described with respect to urinary catheters, it is to be understood that other types of catheters, e.g., tracheal catheters, venous catheters, etc. operate on similar principles and may be manufactured according to the present invention.

As shown in FIG. 3 there is provided mold 30 with first wire 31 and second wire 41 longitudinally aligned with the first wire 31 so that in use follower 32 may slide from first wire 31 to second wire 41. Wire 31 is attached to a suitable source which, as shown in FIG. 3, may be the proximal end 35 of mold 30. First wire 31 terminates at 33 spaced from the proximal end 43 of second wire 41. The follower 32 is again fitted snugly into annular space 36 closely abutted to wire 31 and the inside of mold 30 as described above in the description of FIG. 1. It will be noted that toward the proximal end 35 of mold 30 wire 31 widens so that the proximal end of the catheter produced by the present invention is funnel shaped. It will further be noted by those skilled in the art that the proportions shown in FIG. 3 are not the proportions which would normally be employed in the manufacture of urinary catheters. That is, a typical urinary catheter may be about 16 inches long and about 0.24 inches in diameter. These values are not reflected in FIG. 3 however, for convenience of illustration.

As shown in FIG. 3, at the start of the process the follower 32 is preferably located in annular space 36, a short distance from the widened portion of wire 31. Preferably, the proximal end of the follower 12 is located somewhere along the first 20% of the distance between the distal end of the widened portion and the distal end 34 of the mold 30 and most preferably along the first 1% of this distance. With the wire 31 and follower 32 suitably arranged in mold 30 the material to be molded, which again for purposes of illustration is catalyzed silicone rubber, is injected under pressure by suitable means (not shown) into the proximal end of mold 30. The catalyzed silicone rubber composition may be prepared in the same manner and from the same materials as noted above in the description of the embodiment shown in FIG. 1. Additionally, the silicone rubber is suitably injected into annular space 36 at the same temperatures and pressures described above in connection with the description of FIG. 1.

The catalyzed silicone rubber which has been injected into the mold cavity flows through annular space 36 and pushes follower 32 ahead of it. Eventually the distal end of follower 32 reaches the distal end 33 of wire 31. At this point the follower 32 continues to slide along the wire 31 in response to the pressure of injected silicone rubber. Before the follower 32 disengages completely from the first wire 31 it engages second wire 41 as shown in FIG. 4. The follower 32 then continues along annular passageway 36 until the distal end of the follower reaches the distal end 34 of mold 30. At this point the arrangement of first wire 31, second wire 41, and follower 32 in mold 30 is as shown in FIG. 5.

It will be observed upon reference to FIGS. 4 and 5 that once follower 32 disengages from first wire 31 the silicone rubber injected into the mold 30 may spread throughout the cross section defined by the inner wall of mold 30. As a result a solid tip is provided for the catheter. As shown in FIGS. 3-5 the proximal surfaces of the follower 32 and second wire 41 are concave. Additionally, the follower 32 and second wire 41 are designed so that the transition from the proximal surface of the follower 32 to the second wire 41 is continuous, as shown in FIG. 5. As a result of the above two factors, a desirable smooth rounded tip for the catheter is provided by the present invention.

It will be observed upon reference to FIGS. 3-5 that the distal end 33 of the first wire 31 is preferably rounded so that the catheter will have a continuous smooth inside surface at its distal end. It is to be understood, however, that the shape of the distal end 33 of the first wire 31 may be varied within the scope of the present invention.

After the follower 32 reaches the distal end 35 of mold 30, the molded catheter is cured and stripped from the first wire 31 as described above in connection with the description of FIG. 1. Once the catheter is removed from first wire 31, at least one hole is provided through the tip of the catheter which communicates with the drainage lumen defined by the hollow portion of the catheter. The hole may be provided in a manner well known in the art such as mechanical punching or burning.

It will be appreciated by those skilled in the art that the first wire 31 and follower 32 may be twisted in mold 30 as a result of side stresses caused by the injection of silicone rubber under high pressure. It will further be appreciated that when the first and second wires are cylindrical and concentric with the inside walls of mold 30, then the twisting will not substantially affect the transfer of follower 32 from first wire 31 to second wire 41 since, even after being twisted, the cylindrical first wire 31 will still be concentrically disposed and therefore aligned with second wire 41 within the mold 30. However, when the first wire 31 and second wire 41 are not cylindrical and concentric with the inside walls of the mold cavity, a severe problem may be created if first wire 31 is twisted in the mold as a result of the fluid pressure in the mold cavity. The problem created is that when wire 31 is twisted then follower 32 is also twisted and is therefore no longer aligned with second wire 41. As a result, unless the follower 32 and second wire 41 are especially designed as hereinafter described, the follower 32 will not slide from the first wire 31 onto second wire 41.

Figure 6:
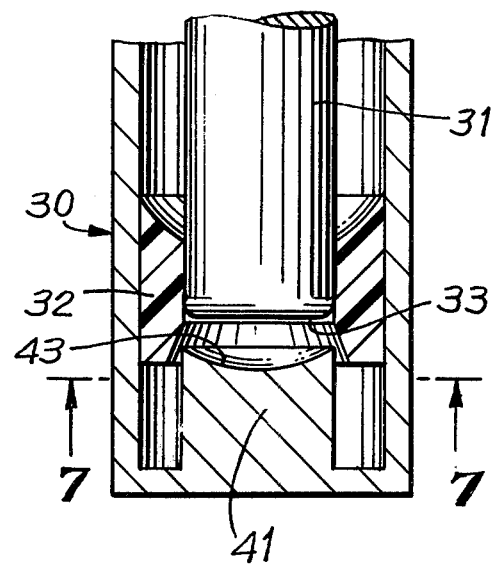
FIG. 6 shows the arrangement of the follower and wires at yet another stage of one embodiment of my invention.
Figure 7:
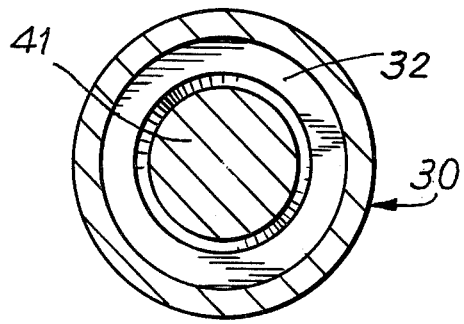
FIG. 7 shows a cross section of FIG. 6 along line 7—7.

Referring now to FIGS. 6 and 7 there is shown a longitudinal side view and cross sectional view of the arrangement of first wire 31, second wire 41, and follower 32 in mold 30 at the instant the follower 32 begins to engage second wire 41. As seen from FIGS. 6 and 7, the inside wall of follower 32 tapers gradually outwardly at least at the distal portion of the follower so that at the point where follower 32 begins to engage second wire 41 the cross sectional area defined by the inner wall of the distal end 37 of follower 32 is larger than the cross sectional area defined by the proximal end 43 of the second wire 41. As a result, even if the follower 32 and second wire 41 are somewhat out of alignment they will still engage with each other and align themselves gradually as the follower travels toward the distal end 34 of mold 30.

It will be recalled that it was earlier noted that substantial alignment problems do not occur when the wire is cylindrical and concentric with the mold wall as is shown in FIGS. 6 and 7. However, even when the wire appears cylindrical and concentric with the mold as shown in FIGS. 6 and 7, it is still preferred that the follower and second wire be designed as shown in FIGS. 6 and 7 since the wires may not be perfectly concentric or cylindrical or the wires may be somewhat distorted by the twisting described above.

As noted above, the cross sectional area defined by the inner wall of the distal end 37 of follower 32 is preferably larger than the area defined by the proximal end 43 of the second wire 41. As used herein, when it is said that one cross sectional area is greater than another, it is meant that the smaller cross sectonal area may be superimposed entirely within the larger cross sectional area as is shown in FIG. 7.

Figure 8:
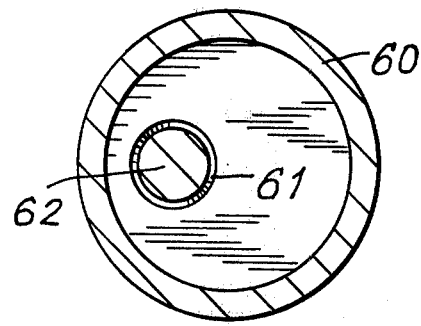
FIG. 8 shows the relationship of follower to the second wire in one embodiment of my invention.
Figure 9:
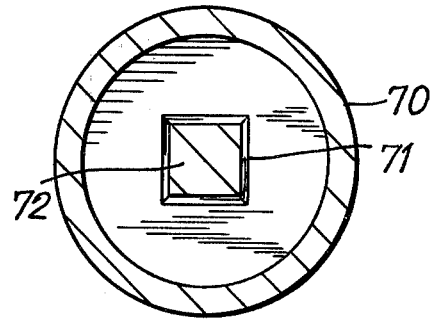
FIG. 9 shows the relationship of the follower to the second wire in another embodiment of my invention.

Referring now to FIGS. 8 and 9 there are illustrated two other examples where the cross sectional area defined by the inner wall of the distal end of a follower is greater than the cross sectional area defined by the proximal end of the second wire. As in FIG. 7, the views shown in FIGS. 8 and 9 are taken along a line through the proximal end of the second wire. In FIG. 8 there is shown mold 60 in which there is a non-concentric cylindrical second wire 62 aligned with a first wire not shown and follower 61. As shown in FIG. 8, the cross sectional area defined by the proximal end of second wire 62 does not cross or touch the cross sectional area defined by the inner wall of the follower 61 at its distal end. Therefore, as defined above, the cross sectional area defined by the proximal end of the second wire 62 is smaller than the cross sectional area defined by the inner wall of follower 61 at its distal end.

In FIG. 9 there is shown mold 70 in which there is a wire 72 with a square cross section and follower 71. Again, as shown, the cross sectional area defined by the second wire 72 is smaller than the cross sectional area defined by the inner walls of the follower at its distal end.

It should be recognized that the differences in cross sectional area as shown in FIGS. 7 to 9 are exaggerated for the purposes of illustration. In practice, in appropriate circumstances the cross sectional areas may only differ from each other slightly, e.g., on the order of a few thousandths of a square inch.

While the preferred embodiments described above have employed catalyzed silicone rubber, it is to be understood that any material that may be injection molded may be employed in the apparatus and process of the present invention. These materials may be thermoplastic polymers, thermosetting polymers or other moldable materials. A particularly desirable class of thermosetting polymers are heat curable elastomers. Examples of thermoplastic polymers that may be employed in the present invention include polyethylene, polypropylene, vinyl polymers and copolymers, polystyrene, nylon, acrylonitrile butadiene styrene and thermoplastic polyesters. Examples of thermosetting polymers, in addition to silicone rubbers, include natural rubber, other synthetic rubbers, polyurethane, thermosetting polyesters and expoxies. Examples of other moldable materials include, but are not limited to wax, asphalt, plaster, concrete, glass and metals. It is to be understood that the properties of the above materials are well known in the art and it is within the purview of those skilled in the art to cause said materials to flow and set in a mold cavity as required in my process.

It is also to be understood that a plurality of hollow articles, in addition to the ones described above, may be made by the process and apparatus of my invention. Other medical devices that may be made include trocar catheters, endotracheal tubes, traceostomy tubes, and drainage tubes with specially shaped ends. Other non-medical devices that may be made include tubular connectors for recirculating the exhaust gases of internal combustion engines, tubular connectors for emergency oxygen supply systems on commercial aircraft, hoses with specially shaped ends for use in dishwashing machines and tubular connectors for circulating fluids in office duplicating machines.

My invention may also be employed to produce articles much larger or smaller than those described above. Examples of larger articles include vacuum cleaner hose and sewer pipe sections. It is therefore to be understood that the wires employed according to the present invention may have cross sectional areas on the order of anywhere between a few thousandths of a square feet or more.

It is further to be understood that articles that have nonlinear longitudinal center lines may be produced by the process and apparatus of the present invention. In this embodiment of the invention a curved wire is provided in a mold with a curved inside wall.

Further, it is to be understood that a second wire is not required in order to obtain hollow articles with a solid tip. Rather, the mold cavity may be designed so that the follower slides off the first wire and then slides by itself the rest of the way to the distal end of the mold cavity. It is apparent, however, that in this embodiment material being molded will flow into the hole of the follower to provide a "pigtail". As a result, a smooth tip will not be directly obtained. However, in this embodiment a smooth tip may be subsequently provided, e.g., by clipping the pigtail and polishing the tip.

It is additionally to be understood that molds and wires of varying cross sectional area may be employed according to the present invention. For example, the mold cavity may be enlarged along a portion of the longitudinal distance traversed by the follower in the mold cavity. In this embodiment, the length of the enlarged portion of the mold is smaller than the longitudinal length of the follower so that in operation the follower will span the enlarged portion of the mold cavity and always maintain contact in close abutment with a portion of the inside wall of the mold.

Finally, it is to be understood that articles with more than one hollow channel may be produced according to the present invention. For example, two wires may be positioned in the mold in parallel arrangement and the follower provided with two holes in order to obtain a hollow article with two parallel channels.

It is therefore to be understood that while the invention has been described with respect to preferred embodiments, variations may be perceived by those skilled in the art while nevertheless not departing from the scope of my invention as described by the claims appended hereto.

I claim:

1. The process of manufacturing a catheter which comprises:
   a. providing a mold with a first wire longitudinally disposed therein, said first wire having a widened cross-section at its proximal end;
   b. providing a second wire spaced distally from said first wire and longitudinally aligned therewith;
   c. positioning a follower about the first wire on close abutment with both the first wire and inside of the mold, said follower maintaining the first wire spaced from the inside wall of the mold so as to define an annular space between the first wire and the inside of the mold, said follower being initially positioned proximally of the distal end of the mold and distally of the widened cross-section of the wire;
   d. introducing a molding material into said annular space proximally of the proximal side of said follower under a pressure sufficient to distally displace said follower whereby molding material is molded around the widened and unwidened portions of the first wire;
   e. continuing to introduce said molding material into said mold until said follower is displaced off said first wire and onto said second wire whereby there is formed a catheter including a drainage lumen, a funnel and a catheter tip;
   f. stripping the resulting catheter from the first wire; and
   g. providing at least one hole at the distal end of the catheter in communication with said drainage lumen.

2. The process of claim 1 wherein the distal end of the follower positioned in step c) is proximal of the distal end of said first wire.

3. The process of claim 1 wherein the molding material is catalyzed silicone rubber.

4. The process of claim 1 which further comprises maintaining said mold at a temperature sufficient to partially cure said material as it distally displaces the follower in the mold.

5. The process of claim 1 wherein the proximal end of said follower is initially located in the first 20% of the mold.

6. The process of claim 1 wherein the proximal end of said follower is initially located in the first 20% of the mold between the distal end of the widened portion of the wire and the distal end of the mold.

7. The process of claim 1 wherein the catheter is expanded by soaking it in an organic solvent before it is stripped from the wire.

8. The process of claim 1 wherein the cross sectional area defined by the inside wall of the distal end of said follower is larger than the cross sectional area defined by the proximal end of said second wire.

9. The process of claim 1 wherein the proximal ends of said follower and second wire are concave, so as to provide a catheter with a rounded tip.

* * * * *

UNITED STATES PATENT AND TRADEMARK OFFICE
CERTIFICATE OF CORRECTION

PATENT NO. : 4,005,166
DATED      : January 25, 1977
INVENTOR(S): James R. Quick It is certified that error appears in the above-identified patent and that said Letters Patent are hereby corrected as shown below:

In Column 8, line 45, -- inch to several square -- should be inserted after "square".

Signed and Sealed this

Twenty-sixth Day of April 1977

[SEAL]

Attest:

RUTH C. MASON
*Attesting Officer*

C. MARSHALL DANN
*Commissioner of Patents and Trademarks*